(12) United States Patent
Chen et al.

(10) Patent No.: US 12,175,616 B2
(45) Date of Patent: Dec. 24, 2024

(54) METHOD FOR REAL-TIME POSITIONING COMPENSATION OF IMAGE POSITIONING SYSTEM AND IMAGE POSITIONING SYSTEM CAPABLE OF REAL-TIME POSITIONING COMPENSATION

(71) Applicant: METAL INDUSTRIES RESEARCH & DEVELOPMENT CENTRE, Kaohsiung (TW)

(72) Inventors: Chieh-Hua Chen, Kaohsiung (TW); Po-Chi Hu, Kaohsiung (TW); Chin-Chung Lin, Kaohsiung (TW); Wen-Hui Huang, Kaohsiung (TW); Yan-Ting Chen, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 578 days.

(21) Appl. No.: 17/387,287

(22) Filed: Jul. 28, 2021

(65) Prior Publication Data

US 2022/0172445 A1 Jun. 2, 2022

(30) Foreign Application Priority Data

Dec. 1, 2020 (TW) .................................. 109142264

(51) Int. Cl.
*G06T 19/20* (2011.01)
*A61B 34/10* (2016.01)
*A61B 90/00* (2016.01)

(52) U.S. Cl.
CPC .............. *G06T 19/20* (2013.01); *A61B 34/10* (2016.02); *A61B 90/36* (2016.02); *A61B 2090/367* (2016.02); *G06T 2210/41* (2013.01)

(58) Field of Classification Search
CPC ..... G06T 19/20; G06T 2210/41; G06T 19/00; G06T 2210/00; G06T 2207/10012;
(Continued)

(56) References Cited

FOREIGN PATENT DOCUMENTS

EP 3517040 A1 * 7/2019 ............. A61B 6/032
TW 1708591 B 11/2020

OTHER PUBLICATIONS

J. Triboulet, M., et al. "Finding 3D polyhedral object attitude using a virtual model for industrial machining," ETFA 2001. 8th International Conference on Emerging Technologies and Factory Automation. Proceedings (Cat. No.01TH8597), Antibes-Juan les Pins, France (Year: 2001).*

(Continued)

*Primary Examiner* — Manav Seth
(74) *Attorney, Agent, or Firm* — Juan Carlos A. Marquez; Marquez IP Law Office, PLLC

(57) ABSTRACT

An image positioning system capable of real-time positioning compensation includes a 3D marking device, a photographing device, a 3D scanning device, a beam splitter, and a processing unit. The 3D marking device has a polyhedral cube. The beam splitter is configured to cause the photographing device and the 3D scanning device to capture an image of and scan the 3D marking device respectively from the same field of view. The processing unit is configured to calculate image data and 3D scanning data generated respectively by the photographing device and the 3D scanning device to obtain a positioning compensation amount and perform positioning compensation.

9 Claims, 4 Drawing Sheets

(58) Field of Classification Search
CPC . G06T 2207/10116; G06T 2207/10081; G06T 7/70; A61B 34/10; A61B 90/36; A61B 2090/367; A61B 34/00; A61B 90/00; A61B 6/02; A61B 2090/373; A61B 2090/371; A61B 5/1079; A61B 5/0035; A61B 5/0013; A61B 2090/364; A61B 90/361; A61B 2090/3937; A61B 2090/3991; A61B 5/103; A61B 5/065; A61B 2576/00; G06V 2201/034; G01C 11/02

See application file for complete search history.

(56) References Cited

OTHER PUBLICATIONS

Um, Gi-Mun et al. (2011). Multi-view 3D video acquisition using hybrid cameras with beam splitter. 3DTV Conference: The True Vision—Capture, Transmission and Display of 3D Video, 3DTV-CON 2011—Proceedings. 1-4. 10.1109/3DTV.2011.5877216. (Year: 2011).*

* cited by examiner

METHOD FOR REAL-TIME POSITIONING COMPENSATION OF IMAGE POSITIONING SYSTEM AND IMAGE POSITIONING SYSTEM CAPABLE OF REAL-TIME POSITIONING COMPENSATION

CROSS-REFERENCE TO RELATED APPLICATION

This application claims the benefit of Taiwan Patent Application No. 109142264, filed on Dec. 1, 2020, which is hereby incorporated by reference for all purposes as if fully set forth herein.

BACKGROUND

Technical Field

The present disclosure relates to an image positioning technology, and in particular, to a method for real-time positioning compensation of an image positioning system and an image positioning system capable of real-time positioning compensation.

Related Art

TW Patent No. 1708591 discloses a method for 3D real-time positioning for an orthopedic surgery. The method is setting up two photographing devices by fixing a 3D marking device to a surgical site, and setting the two photographing devices as a primary photographing device and a secondary photography device. The two photographing devices are respectively located on two sides of the surgical site. When surgical positioning is to be performed, the primary imaging device captures an image of the 3D marking device, and a computing module determines whether a polyhedral cube of the 3D marking device is shielded. When the polyhedral cube is not shielded, it is determined whether the primary mark is shielded. When the primary mark is not shielded, the primary mark provides space coordinate information. When the primary mark is shielded, three secondary marks are used to calculate the space coordinate information of the primary mark. When the polyhedral cube is shielded, the secondary camera is used to photograph the polyhedral cube through switching, and it is determined whether the primary mark is shielded. When the primary mark is not shielded, the primary mark provides space coordinate information. When the primary mark is shielded, then the three secondary marks are used to calculate the space coordinate information of the primary mark.

The 3D marking device introduces the concept of primary and secondary marks in the above method. When the primary mark is shielded, the space coordinate information of the primary mark may be calculated in real time through the surrounding secondary marks, so as to ensure that the surgical positioning is not affected by the shielding of medical staffs or objects, thereby increasing a freedom degree of a position of medical personnel or objects in an operating room, and reducing restrictions on the movement of medical personnel in the operating room. However, it is inevitable that human error during the operation, such as a collision, changes a positioning origin of the photographing device, and then subsequent positioning is caused to be inaccurate, affecting quality of the operation. In order to ensure that the rest of the operation can proceed smoothly after a positioning error occurs, a method for real-time positioning compensation of an image positioning system and an image positioning system capable of real-time positioning compensation are provided, to urgently solve one of the problems of the image positioning technology.

SUMMARY

An objective of the present disclosure is to provide a method for real-time positioning compensation of an image positioning system and an image positioning system capable of real-time positioning compensation, so that a positioning compensation amount can be obtained by performing calculation on image data and 3D scanning data of a 3D marking device, and then positioning compensation is performed for the image positioning system to improve positioning accuracy of the conventional image positioning system.

Another objective of the present disclosure is to provide a method for real-time positioning compensation of an image positioning system and an image positioning system capable of real-time positioning compensation, so that calculation can be performed on the image data and the 3D scanning data of the 3D marking device in real time online, and the positioning compensation can be quickly performed for the image positioning system, so as to reduce an influence of positioning inaccuracy on an operation procedure.

According to the above objective, the present disclosure provides a method for real-time positioning compensation of an image positioning system, that is, provides an image positioning system capable of real-time positioning compensation configured to position a 3D marking device with a polyhedral cube, wherein the method for real-time positioning compensation of an image positioning system includes: generating, by the image positioning system capable of real-time positioning compensation, image data and 3D scanning data of the 3D marking device from the same field of view (FOV); performing calculation on the image data and the 3D scanning data by using a coordinate transformation matrix, to obtain a positioning compensation amount; and compensating the image positioning system capable of real-time positioning compensation by using the positioning compensation amount.

According to the above objective, the present disclosure further provides an image positioning system capable of real-time positioning compensation, including: a 3D marking device having a polyhedral cube; a photographing device, a 3D scanning device, and a beam splitter, wherein the beam splitter is configured to cause the photographing device and the 3D scanning device to capture an image of and scan the 3D scanning device respectively from the same field of view; and a processing unit configured to perform calculation on image data and 3D scanning data respectively generated by the photographing device and the 3D scanning device, to obtain a positioning compensation amount and perform positioning compensation.

In the present disclosure, the photographing device and the 3D scanning device are used to obtain the image data and the scanning data of the 3D marking device respectively through the beam splitter, the calculation is performed on the image data and the scanning data of the 3D marking device to obtain the positioning compensation amount, and then positioning compensation is performed on the image positioning system, so as to actually improve the positioning accuracy of the conventional image positioning system. In addition, the positioning compensation method of the present disclosure can be performed online in real time, so as to minimize the impact of positioning misalignment of the image positioning system on the operation procedure (for example, a surgical operation).

DETAILED DESCRIPTION

In order to make the above or other objectives, features, and characteristics of the present disclosure more obvious and understandable, the relevant embodiments of the present disclosure are described in detail as follows with reference to the drawings.

Figure 1:
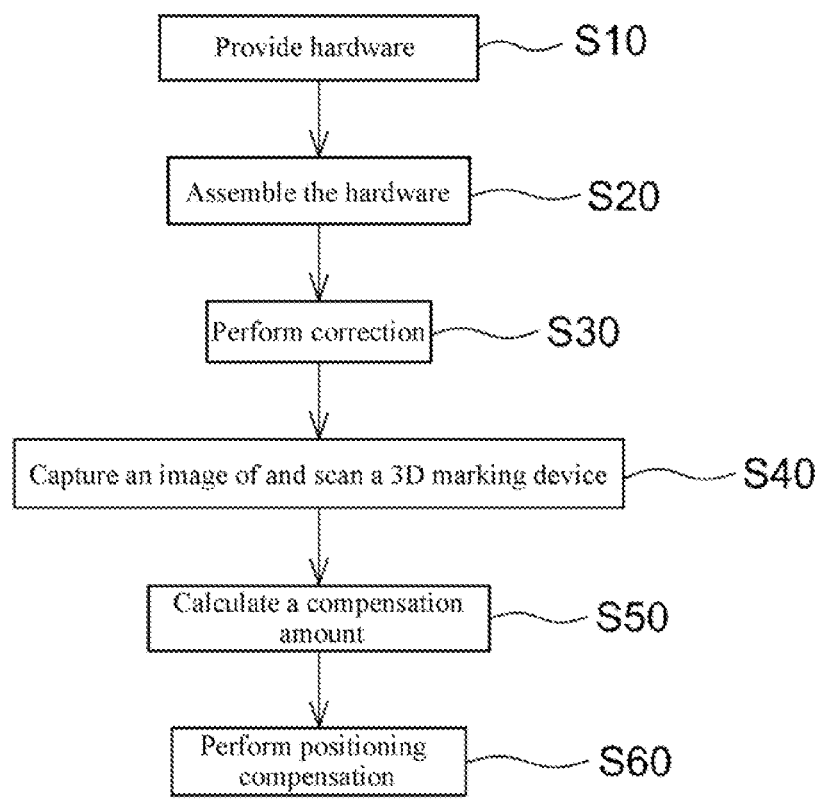
FIG. 1 is a flowchart of steps of an embodiment of a real-time positioning compensation method of an image positioning system according to the present disclosure.
Figure 2:
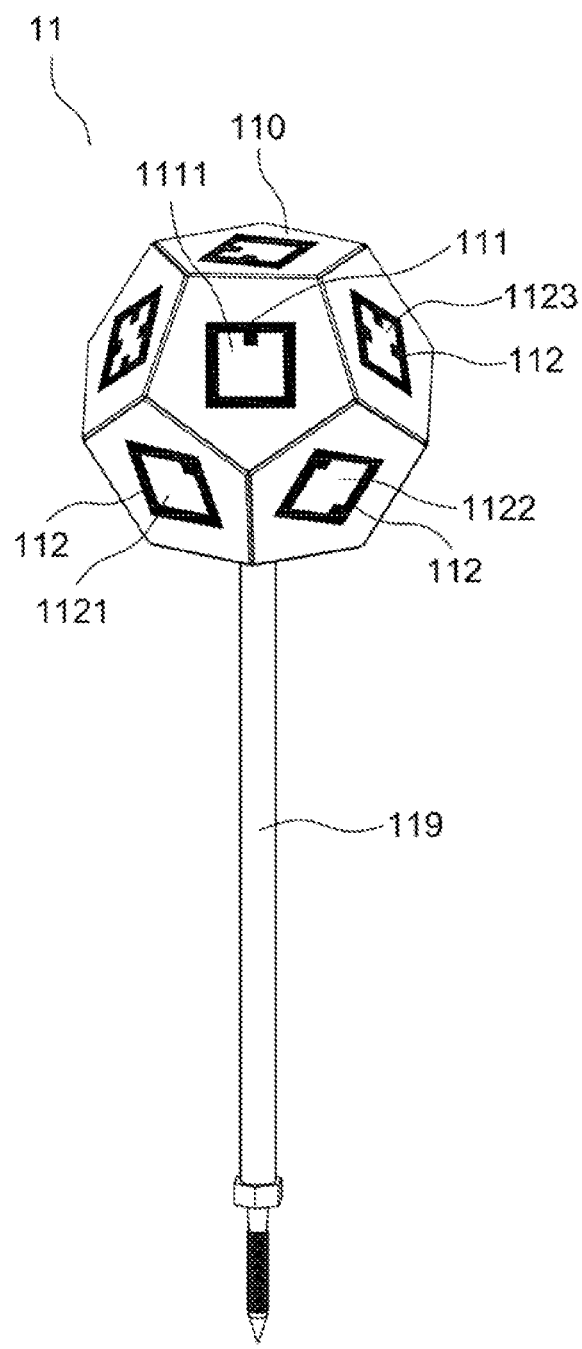
FIG. 2 is a three-dimensional schematic diagram of a 3D marking device according to an embodiment of the present disclosure.
Figure 3:
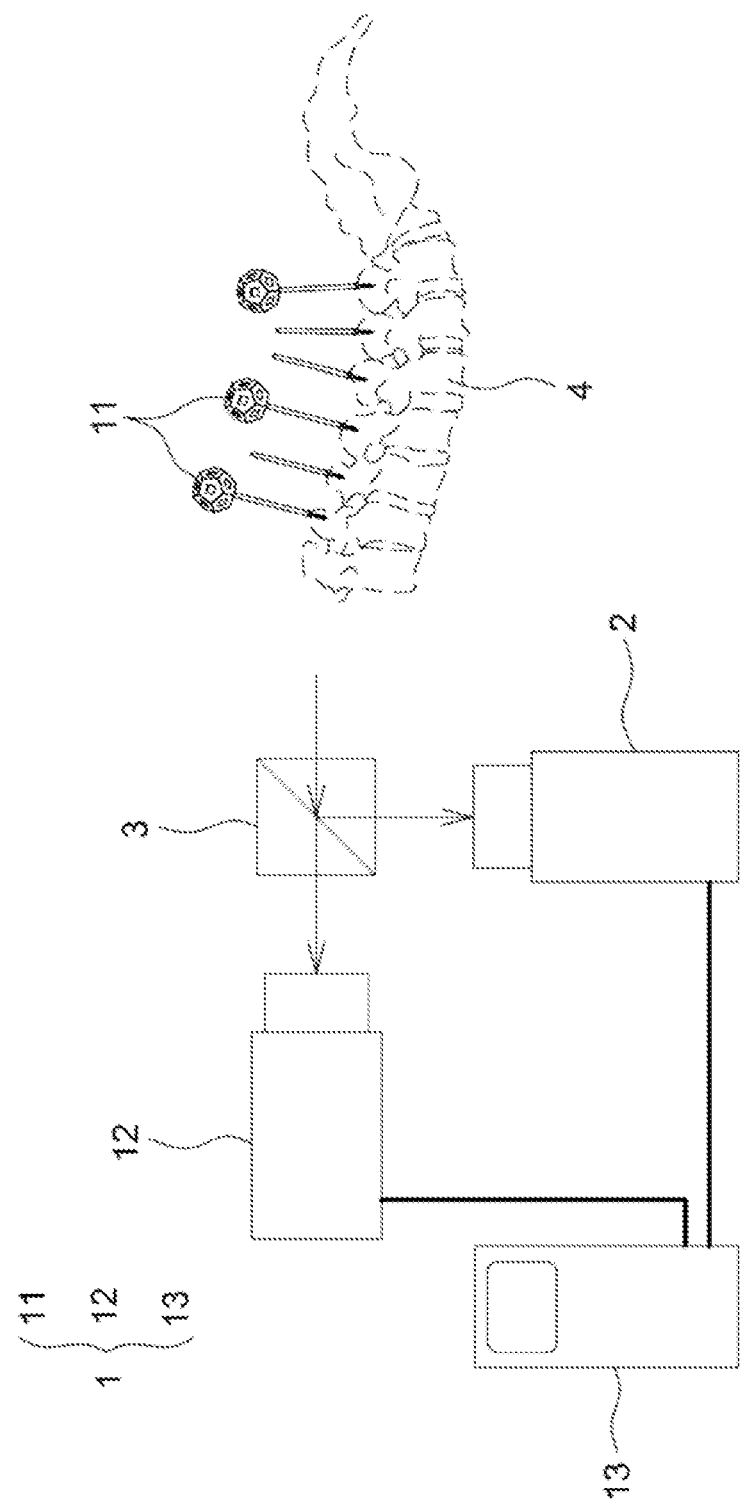
FIG. 3 is a schematic diagram of an image positioning system capable of real-time positioning compensation according to an embodiment of the present disclosure.

FIG. 1 is a flowchart of an embodiment of a method for real-time positioning compensation of an image positioning system according to the present disclosure, FIG. 2 is a three-dimensional schematic diagram of a 3D marking device according to an embodiment of the present disclosure, and FIG. 3 is a schematic diagram of an image positioning system capable of real-time positioning compensation according to an embodiment of the present disclosure. Referring to FIG. 1, an embodiment of the method for real-time positioning compensation of the image positioning system of the present disclosure includes: step (S10) of providing hardware; step (S20) of assembling the hardware; step (S30) of performing correction); step (S40) of capturing an image of and scanning a 3D marking device); step (S50) of calculating a compensation amount); and step (S60) of performing positioning compensation).

Referring to FIG. 1, FIG. 2, and FIG. 3 together, the step (S10) of providing the hardware is providing an image positioning system 1, a 3D (i.e., three-dimensional) scanning device 2, and a beam splitter 3. The image positioning system 1 includes at least one 3D (i.e., three-dimensional) marking device 11, a photographing device 12, and a processing unit 13.

The at least one 3D marking device 11 is used to mark a to-be-positioned operation site 4, and each 3D marking device 11 includes: a polyhedral cube 110 and a nail-shaped body 119 physically connected to the polyhedral cube 110. The polyhedral cube 110 includes at least four faces (e.g., facets), and the at least four faces respectively serve as a primary mark 111 and a plurality of secondary marks 112. For example, the polyhedral cube 110 shown in FIG. 2 includes twelve faces, that is, the polyhedral cube 110 is a twelve-face cube, and the plurality of secondary marks 112 is ten secondary marks. The primary mark 111 includes a primary graphic code 1111. Three secondary marks 112 respectively include a first secondary graphic code 1121, a second secondary graphic code 1122, and a third secondary graphic code 1123. The primary graphic code 1111 is used to provide space coordinate information and calculate 6 degree of freedom (DOF) posture data. For example, an object has 6 DOF in space, that is, a DOF of movement in directions of the three rectangular coordinate axes of X, Y, and Z and a DOF of rotation around the three coordinate axes. The primary graphic code 1111 and the first to third secondary graphic codes 1121, 1122, 1123 are different quick response codes (i.e., QR Code). The nail-shaped body 119 is used to be fixed to the to-be-positioned operation site (4). When the operation site 4 is a spine, the spike-shaped body 119 is a spine spike. In this embodiment, a number of adopted 3D marking devices 11 is 3.

The photographing device 12 (e.g., camera) has an image capturing unit, e.g., CMOS or CCD image sensor (not shown) for photographing an optical image of the 3D marking device 11 and converting the optical image to a digital signal. The processing unit 13 is a processor with calculation functions and is configured to process image data and 3D scanning data of the 3D marking device 11 and perform positioning compensation.

The 3D scanning device 2 (e.g., 3D scanner) has at least one image capturing unit, e.g., CMOS or CCD image sensor (not shown) and a projection light source (such as an infrared ray, not shown). The projection light source projects a light beam on the 3D marking device 11. The image capturing unit captures the light beam reflected from the 3D marking device 11 to obtain image data on a geometric surface of the 3D marking device 11.

Referring to the FIG. 1 and FIG. 3 together, the step (S20) of assembling the hardware includes: fixing the 3D marking device 11 to the operation site 4; and setting up the photographing device 12, the 3D scanning device 2, and the beam splitter 3. In this embodiment, the operation site 4 is the spine, and three 3D marking devices 11 are fixed to the spine by using the spike-shaped body 119 (that is, the spine spike). In the set-up of the photographing device 12, the 3D scanning device 2, and the beam splitter 3, an optical path of the photographing device 12 is perpendicular to and intersects an optical path of the 3D scanning device 2, where the beam splitter 3 is disposed at an intersection of the two optical paths, so that the photographing device 12 and the 3D scanning device 2 can have the same field of view (FOV). In terms of the set-up manner of the photographing device 12 and the 3D scanning device 2 shown in FIG. 3, the photographing device 12 is assembled to a beam penetrating end of the beam splitter 3, and the 3D scanning device 2 is assembled to a beam reflecting end of the beam splitter 3. However, the set-up manner of the photographing device 12 and the 3D scanning device 2 of the present disclosure is not limited thereto, and the set-up positions of the photographing device 12 and the 3D scanning device 2 may also be transposed, that is, the 3D scanning device 2 is assembled to the beam penetrating end of the beam splitter 3, and the photographing device 12 is assembled to the beam reflecting end of the beam splitter 3.

Referring to FIG. 1, the step (S30) of performing correction is correcting the photographing device 12 and the 3D scanning device 2 to improve the accuracy of capturing the optical image and the image data on the geometric surface of the 3D marking device 11. There are many correction methods for the disclosed photographing device 12 and 3D scanning device 2, and those familiar with the art can choose a suitable correction method according to actual needs.

Referring to FIG. 1 and FIG. 3 together, the step (S40) of capturing the image of and scanning the 3D marking device is respectively obtaining the image data and the 3D scanning data of the 3D marking device 11 by the photographing device 12 and the 3D scanning device 2. The step includes: adjusting the photographing device 12, the 3D scanning device 2, and the beam splitter 3, so that the 3D marking device 11 can enter the field of view (FOV); capturing an image of the 3D marking device 11 by the photographing device 12, to obtain digital image data of the 3D marking device, and transmitting the image data to the processing unit 13; and projecting a light beam on the 3D marking device 11 by the projection light source of the 3D scanning device 2, capturing the light beam reflected from the 3D marking device 11 by the image capturing unit of the 3D scanning device 2, to obtain the 3D scanning data of the 3D marking device 11 (that is, the image data on the geometric surface of the 3D marking device), and transmitting the 3D scanning data to the processing unit 13.

Referring to FIG. 1, the step (S50) of calculating the compensation amount is performing, by the processing unit 13, the calculation on the image data and the 3D scanning data of the 3D marking device 11 to obtain the positioning compensation amount of the image positioning system 1. After the processing unit 13 obtains the image data from the photographing device 12, the posture data of the 3D marking device 11 may be calculated according to the space coordinate information provided by the primary graphic code 1111 of the primary mark 111 of the 3D marking device 11. When the primary mark 111 is shielded, the processing unit 13 may calculate the space coordinate information of the primary marker 111 by using the first secondary graphic code 1121, the second secondary graphic code 1122, and the third secondary graphic code 1123 of the three secondary marks 112, and calculate the posture data of the 3D marking device 11. Next, the processing unit 13 calculates the positioning compensation amount of the image positioning system 1 by using the posture data and the 3D scanning data of the 3D marking device 11.

The image data of the 3D marking device 11 is captured by the photographing device 12, and the 3D scanning data is obtained by the 3D scanning device 2. Therefore, the process of calculation of the posture data and the 3D scanning data of the 3D marking device 11 involves conversion of different coordinate systems. Equations for relevant transformation are listed below:

$$T_{c,m} = T_{c,cb} \times T_{cb,m}$$

$$T_{cb,m} = T_{c,cb}^{-1} \times T_{c,m}$$

Wherein:

$T_{c,m}$ represents a transformation matrix between the 3D marking device 11 and the photographing device 12 (that is, the image positioning system 1).

$T_{c,cb}$ represents a transformation matrix between a coordinate system of the photographing device 12 (that is, the image positioning system 1) and a coordinate system of the 3D scanning device 2.

$T_{cb,m}$ represents a transformation matrix between the 3D marking device 11 and the coordinate system of the 3D scanning device 2.

$T_{c,cb}^{-1}$ represents an inverse matrix of the transformation matrix between the coordinate system of the photographing device 12 (that is, the image positioning system 1) and the coordinate system of the 3D scanning device 2.

A compensation transformation matrix between the 3D marking device 11 and the photographing device 12 (that is, the image positioning system 1):

$$T_{c,m}' = T_{c,m} \times T_{cb,m}'$$

Wherein:

$T_{c,m}'$ represents a compensation transformation matrix between the 3D marking device 11 and the photographing device 12 (that is, the image positioning system 1).

$T_{cb,m}'$ represents an alignment-transformation matrix between the 3D marking device 11 and the 3D scanning device 2.

In other words, when $T_{cb,m}$ is obtained through calculation, the alignment of the 3D scanning device 2 is performed, that is, the 3D marking device 11 is aligned to the 3D scanning device 2, and at this point, the alignment-transformation matrix $T_{cb,m}'$ is obtained through calculation. From the above equation, the compensation transformation matrix $T_{c,m}'$ between the 3D marking device 11 and the photographing device 12 (that is, the image positioning system 1) can be obtained.

Referring to FIG. 1, the step (S60) of performing the positioning compensation is performing positioning compensation on the image positioning system 1 according to the positioning compensation amount obtained through calculation in the step (S50) of calculating the compensation amount.

Figure 4:
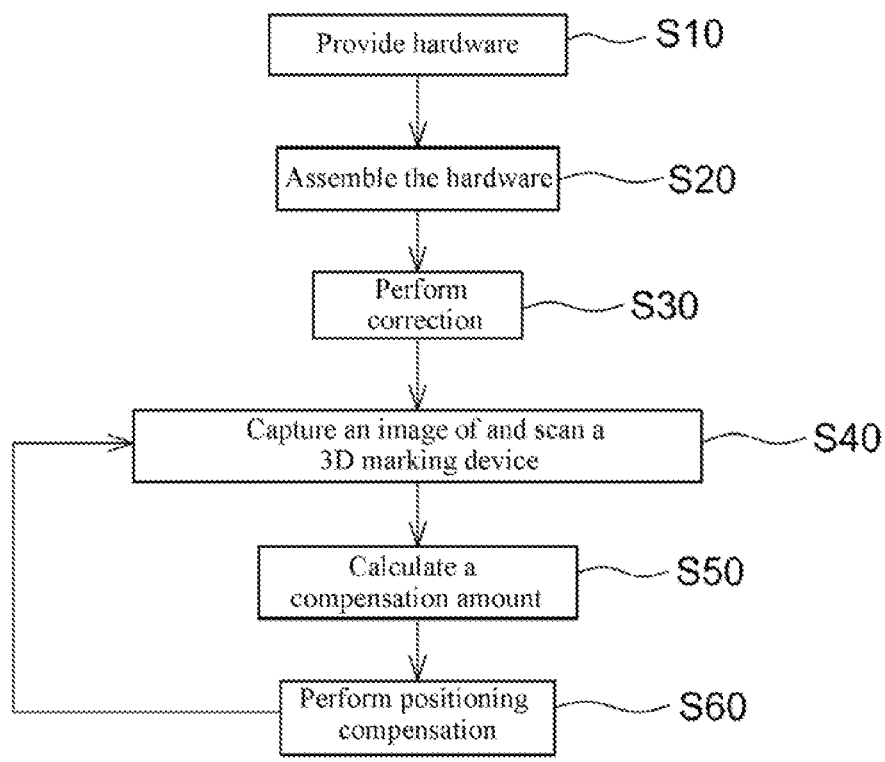
FIG. 4 is a flowchart of steps of another embodiment of a method for real-time positioning compensation of the image positioning system according to the present disclosure.

The above method for real-time positioning compensation of an image positioning system is adapted to be performed at the beginning of an operation procedure (for example, a surgical operation), to ensure the accuracy of instrument positioning during the operation procedure and improve operation quality of the operation procedure. In the midway of the operation procedure, the photographing device in the image positioning system may be moved due to human error (such as collision). In this case, as long as the step (S40) of capturing an image of and scanning the 3D marking device, the step (S50) of calculating the compensation amount, and the step (S60) of performing positioning compensation are performed again (referring to FIG. 4), the operation procedure may be performed quickly again, so as to minimize the impact of human error on the operation procedure. If the 3D marking device is moved or even falls off due to man-made collisions, the step (S20) of assembling the hardware may be performed to fix the moved or fallen 3D marking device to the operation site again, and then the step (S30) of performing correction, the step (S40) of capturing an image of and scanning the 3D marking device, the step (S50) of calculating the compensation amount, and the step (S60) of performing positioning compensation are performed, so that the positioning compensation of the image positioning system can be completed in real time.

In addition, referring to FIG. 3, the present disclosure provides an image positioning system capable of real-time positioning compensation, including: a 3D marking device 11 configured for being fixed to a to-be-positioned operation site 4, wherein the 3D marking device 11 has a polyhedral cube 110; a photographing device 12 configured to capture an image of the 3D marking device 11 to obtain image data of the 3D marking device; a 3D scanning device 2 configured to scan the 3D marking device 11 to obtain 3D scanning data of the 3D marking device; a beam splitter 3, wherein an optical path of the photographing device 12 is perpendicular to and intersects an optical path of the 3D scanning device 2, and the beam splitter 3 is disposed at an intersection of the two optical paths, so that the photographing device 12 and the 3D scanning device 2 have the same field of view (FOV); and a processing unit 13 configured to perform calculation on the image data and the 3D scanning data of the 3D marking device 11 and perform positioning compensation.

In the present disclosure, the photographing device and the 3D scanning device are used to obtain the image data and the scanning data of the 3D marking device respectively through the beam splitter, the calculation is performed on the image data and the scanning data of the 3D marking device to obtain the positioning compensation amount, and then positioning compensation is performed on the image positioning system, so as to actually improve the positioning accuracy of the conventional image positioning system. In addition, the positioning compensation method of the present disclosure can be performed online in real time, so as to minimize the impact of positioning misalignment of the image positioning system on the operation procedure (for example, a surgical operation).

Based on the above, only the preferred implementations or embodiments of the technical means adopted by the present disclosure for solving the problems are described, and are not intended to limit the scope of patent implementation of the present disclosure. That is, all equivalent changes and modifications made in accordance with the scope of the patent operation of the present disclosure or made in accordance with the scope of the patent of the present disclosure fall within the scope of the patent of the present disclosure.

What is claimed is:

1. A method for real-time positioning compensation of an image positioning system, comprising the following steps of:
providing an image positioning system configured to position a 3D marking device having a polyhedral cube;
generating, by a photographing device and a 3D scanning device of the image positioning system, image data and 3D scanning data of the 3D marking device from the same field of view (FOV);
performing calculation on the image data and the 3D scanning data by using a coordinate transformation matrix, to obtain a positioning compensation amount; and
compensating the image positioning system by using the positioning compensation amount;
wherein in the step of performing the calculation on the image data and the 3D scanning data by using the coordinate transformation matrix, and the positioning compensation amount is obtained by using the following equations:

$$T_{c,m} = T_{c,cb} \times T_{cb,m};$$

$$T_{cb,m} = T_{c,cb}^{-1} \times T_{c,m};$$

$$T_{c,m}' = T_{c,m} \times T_{cb,m}',$$

wherein:
$T_{c, m}$ represents a transformation matrix between the 3D marking device and the photographing device;
$T_{c, cb}$ represents a transformation matrix between a coordinate system defined by the photographing device and a coordinate system defined by the 3D scanning device;
$T_{cb, m}$ represents a transformation matrix between the 3D marking device and the coordinate system defined by the 3D scanning device;
$T_{c, cb-1}$ represents an inverse matrix of the transformation matrix between the coordinate system defined by the photographing device and the coordinate system defined by the 3D scanning device;
$T_{c, m}'$ represents a compensation transformation matrix between the 3D marking device and the photographing device; and
$T_{cb, m}'$ represents an alignment-transformation matrix between the 3D marking device and the 3D scanning device.

2. The method for real-time positioning compensation of an image positioning system according to claim 1, wherein the image positioning system obtains the image data and the 3D scanning data from the same field of view by means of a beam splitter.

3. The method for real-time positioning compensation of an image positioning system according to claim 2, wherein the image positioning system further comprises a photographing device and a 3D scanning device, an optical path of the photographing device is perpendicular to and intersects an optical path of the 3D scanning device, and the beam splitter is disposed at an intersection of the two optical paths.

4. The method for real-time positioning compensation of an image positioning system according to claim 3, wherein before the step of generating, by the image positioning system, the image data and the 3D scanning data, the method further comprises a step of correcting the photographing device and the 3D scanning device.

5. The method for real-time positioning compensation of an image positioning system according to claim 1, wherein after the step of compensating the image positioning system by using the positioning compensation amount, the method further comprises all of the steps in claim 1 that are further performed again.

6. An image positioning system using the method for real-time positioning compensation of the image positioning system of claim 1, comprising:
a 3D marking device having a polyhedral cube;
a photographing device, a 3D scanning device, and a beam splitter, wherein the beam splitter is configured to cause the photographing device and the 3D scanning device to capture an image of and scan the 3D scanning device respectively from the same field of view (FOV); and
a processing unit configured to perform calculation on image data and 3D scanning data respectively generated by the photographing device and the 3D scanning device, to obtain a positioning compensation amount and perform positioning compensation.

7. The image positioning system according to claim 6, wherein an optical path of the photographing device is perpendicular to and intersects an optical path of the 3D scanning device, and the beam splitter is disposed at an intersection of the two optical paths, so that the photographing device and the 3D scanning device have the same field of view.

8. The image positioning system according to claim 6, wherein the photographing device is disposed at a beam penetrating end of the beam splitter, and the 3D scanning device is disposed at a beam reflecting end of the beam splitter.

9. The image positioning system according to claim 6, wherein the polyhedral cube comprises at least four faces, wherein the at least four faces respectively serve as a primary mark and a plurality of secondary marks, wherein the primary mark is configured to provide space coordinate information, and when the primary mark is shielded, the processing unit calculates the space coordinate information of the primary mark by using the plurality of secondary marks.

* * * * *